United States Patent [19]

Chaudhuri et al.

[11] Patent Number: 5,160,528

[45] Date of Patent: *Nov. 3, 1992

[54] DELIVERY SYSTEM FOR AGRICULTURAL CHEMICALS

[75] Inventors: Ratan K. Chaudhuri, Butler; Kolazi S. Narayanan, Palisades Park; Manilal Dahanayake, Wayne, all of N.J.

[73] Assignee: ISP Investments Inc., Wilmington, Del.

[*] Notice: The portion of the term of this patent subsequent to Dec. 10, 2008 has been disclaimed.

[21] Appl. No.: 505,030

[22] Filed: Apr. 5, 1990

Related U.S. Application Data

[63] Continuation-in-part of Ser. No. 448,707, Dec. 11, 1989, Pat. No. 5,071,463.

[51] Int. Cl.$^5$ .................... A01N 57/00; A01N 43/00; A01N 43/48; A01N 43/40; A01N 37/00; A01N 37/34; A01N 37/10; A01N 37/18; A01N 47/28; A01N 33/02; A01N 31/00; A01N 25/00

[52] U.S. Cl. .................................. 71/79; 71/86; 71/88; 71/93; 71/94; 71/100; 71/105; 71/107; 71/118; 71/119; 71/121; 71/124; 514/788

[58] Field of Search .............. 514/408, 424, 936, 946, 514/947, 788; 71/DIG. 1, 93, 79, 86, 88, 94, 100, 105, 107, 118, 119, 121, 124

[56] References Cited

U.S. PATENT DOCUMENTS

| | | | |
|---|---|---|---|
| 3,479,176 | 11/1969 | Forrest | 71/94 |
| 3,882,243 | 5/1975 | Maeda et al. | 514/552 |
| 4,122,170 | 10/1978 | Rajadhyaksha | 514/24 |
| 4,444,762 | 4/1984 | Rajadhyaksha | 514/24 |
| 4,525,199 | 6/1985 | Rajakhyaksha | 71/65 |
| 4,638,026 | 1/1987 | Sambuis | 524/98 |
| 4,762,549 | 8/1988 | Rajadhyaksha | 71/88 |
| 4,840,663 | 1/1989 | Quadranti et al. | 71/93 |

FOREIGN PATENT DOCUMENTS 2128225 12/1972 Fed. Rep. of Germany.

OTHER PUBLICATIONS

Chemical Abstracts (75:109261K) 1971.
Chemical Abstracts (78:80918d) 1973.
Chemical Abstracts (111:111041u) 1989.
Research Disclosure Dec. 1989 "Stable Pesticidal Emulsions".

Primary Examiner—Frederick E. Waddell
Assistant Examiner—K. Weddington
Attorney, Agent, or Firm—Jules Goldberg; Joshua J. Ward; Marilyn J. Maue

[57] ABSTRACT

An emulsifiable concentrate comprising an agriculturally active chemical, a surfactant, an organic diluent and a solvent having a component capable of solubilizing the agriculturally active chemical and, in conjunction with the surfactant, being effective to disperse the agriculturally active chemical. The inventive concentrate allows for high concentrations of the active ingredient, exhibits excellent stability and produces highly stable compositions upon dilution with water.

13 Claims, No Drawings

DELIVERY SYSTEM FOR AGRICULTURAL CHEMICALS

CROSS-REFERENCE TO OTHER APPLICATIONS

This application is a continuation-in-part of application Ser. No. 07/448,707, filed Dec. 11, 1989; now U.S. Pat. No. 5,071,463 the contents of which are incorporated herein by reference.

BACKGROUND OF THE INVENTION

I. Field of the Invention

The invention relates to a delivery system for agriculturally active chemicals. More particularly, the invention relates to an emulsifiable concentrate of difficult to dissolve agricultural chemicals.

II. Description of the Prior Art

Agricultural chemicals are most preferably applied in the form of aqueous emulsions, solutions, or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into an emulsion, it is difficult to maintain the emulsified state. This makes it difficult to maintain a uniform formulation, particularly, when the formulation is diluted with water for application to the plants.

Typically, for example, the agriculturally active ingredient is mixed with one or more of a variety of conventional solvents and an emulsifying agent to form a concentrate. This concentrate may be an emulsion, suspension, or solution. The concentrate is then stored until it is transported to the site of use or may simply be transported and stored at the site of use. In any event, the concentrate normally will undergo some period of storage until it is ready for use. Understandably, it is most desirable to be able to transport the agriculturally active ingredient at the highest concentration possible so as to minimize the volume of material which need be transported. By the same token, however, at the use site, it is normally not feasible to admix ingredients together or to process them other than to dilute the concentrate with water. Accordingly, it is important that the concentrate emulsify easily, i.e., exhibit good "bloom", upon the addition of water. In addition, at the use site, it is often necessary to store the diluted concentrate for extended time periods until the actual application to the plants. Consequently, it is important that the diluted form of the concentrate exhibit good stability with respect to the uniformity of the emulsion and to avoid precipitation of the active ingredients. If non-uniformity or precipitation occurs in the diluted form, then non-uniformity will result in the application of the diluted formulation to the plants.

An attempt to provide concentrates of agriculturally useful chemicals is disclosed in South African patent application No. 695,393, filed Jul. 25, 1969. This application is directed to the formulation of a concentrate substantially water-insoluble pesticides for agricultural use. The pesticides, either in oil or solid form, are mixed with pyrrolidones having a hydrogen or a lower alkyl group containing from 1 to 4 carbon atoms attached to the nitrogen atom of the pyrrolidone ring. The application discloses that concentrated solutions of difficult to dissolve pesticides could be formulated and that such concentrates exhibited good stability. The concentrates utilized are those containing the pesticidal active ingredient, the particular lower alkyl pyrrolidone, a co-solvent which is usually a common organic solvent, such as, an aromatic including xylene, methylated and polyalkylated naphthalenes and aliphatic solvents, and a dispersing or emulsifying agent, such as, a surfactant, including polyoxyethylene alkylphenols, polyoxyethylene fatty esters, polyoxyethylene sorbitan fatty esters which may be blended with oil-soluble sulfonates, calcium and aminosulfonate salts, and the like.

This prior art does not offer a solution to the problem arising from the difficulty in maintaining the stability of the emulsion after the concentrate is diluted with water. Consequently, unless the diluted form of the concentrate is used immediately after emulsification, it is difficult to provide a stable diluted formulation for application to the plants.

U. S. Pat. No. 4,798,837 discloses an emulsifiable concentrate of the pesticidal compound (CGA):

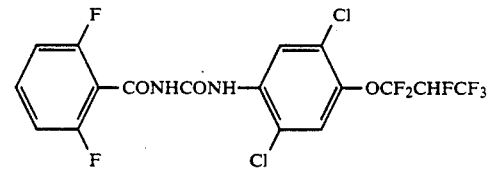

This active concentrate contains 10% of the active ingredient using 30% cyclohexanone as the solvent. However, cyclohexanone is highly toxic. For such agricultural uses, it is desirable to avoid the use of toxic solvents, including those of Lists 1 and 2 of 40 C.F.R. 154.7 dated Apr. 22, 1987, which includes inerts of toxicological concern and solvents having high flash points, as well as to increase the amount of the agriculturally active material in the concentrate.

SUMMARY OF THE INVENTION

We have discovered a novel emulsifiable concentrate of an agriculturally active chemical, which concentrate provides, upon dilution, a highly stable emulsion and avoids precipitation of the active ingredient on extended storage. In addition, the inventive emulsifiable concentrates may contain relatively high concentrations of the agriculturally active ingredient, sometimes referred to as a "loading", making it advantageous from both economic and handling viewpoints. Also, the concentrates of the present invention utilize organic materials which do not pose environmental problems either in use or handling.

More particularly, the emulsifiable concentrate of the present invention is composed of an agriculturally active chemical, a surfactant, an organic diluent, and a hydrophobic solvent having the following Hansens' solubility parameters:

Dispersive component from about 56 to 75%;
Polar component from about 8 to 24%; and
H-bonding component of from about 10 to 30%.

This solvent should also have surfactant properties and act as a non-ionic surfactant with an HLB value ranging from about 2 to 8.

For a discussion of the solubility parameters, see *C.R.C. Handbook of Solubility Parameters and Other Cohesion Parameters*, Allan F.M. Barton, 1983, Table 9, p. 167–170.

DESCRIPTION OF THE PREFERRED EMBODIMENT

As used herein, the term "agriculturally active chemical" includes compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, and the like, as well as any other chemicals having properties which are suitable for agricultural uses in terms of application to plants or domestic uses for controlling insects and pests. Particularly, such chemicals would normally take the form of water-immiscible or oily liquids and/or solids which is substantially insoluble in water. By the term "substantially insoluble", it is meant that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

Suitable agriculturally active chemicals which can be used with the present invention include insecticides, such as, cyclocompounds, carbamates, animal and plant derivatives, synthetic pyrethroids, diphenyl compounds, non-phosphates, organic phosphates, thiophosphates, and dithiophosphates. (See *Agricultural Chemicals*, Book I, *Insecticides*, 1989 Revision by W.T. Thomson, Thomson Publications.) Typical of the insecticides are:

| | |
|---|---|
| cyclocompounds: | 6,7,8,9,10,10-hexachloro-1,5,5a,6,9,9a-hexahydro-6,9-methano-2,4,3-benzodioxathiepin-3-oxide |
| carbamates: | 2-isopropyl phenyl-N-methyl carbamate; |
| | 2-(1,3-dioxolan-2yl) phenylmethyl carbamate; |
| | 2,3-isopropylidine dioxyphenyl methyl carbamate; |
| animal and plant derivatives: | chlorinated hydrocarbons derived from Southern pine; naturally occuring lactone glycoside; |
| synthetic pyrethroids: | (±) α-cyano-3-phenoxybenzyl (±) cis, trans 3-(2,2-dichlorovinyl)-2,2-dimethyl cyclopropane carboxylate; (±) cyano (3-phenoxyphenyl methyl |

-continued

| | |
|---|---|
| | (±)-4-(difluoromethoxy) α-(1-methylethyl) benzene acetate; |
| phenoxy compounds and non-phosphate: | 2,2-bis(p-methoxy phenyl)-1,1,1-trichloroethane; |
| | 1,3,5,tri-n-propyl-1,3,5-triazine-2,4,6 (1H,3H,5H) trione; |
| | ethyl (2E, 4E)-3,7,11-trimethyl-2,4-dodeca dienoate; |
| | 1-decycloxy 4-[(7-oxa-oct-4-ynyl)]-oxybenzene; |
| organic phosphates: | dimethyl phophate ester of 3-hydroxy-N,N-dimethyl-cis-crotonamide; |
| | 2-chloro-1-(2,4-dichloro phenyl) vinyl diethylphosphate; |
| | 4-(methyl thio) phenyl dipropyl phosphate; |
| thiophosphates: | 0,0-diethyl-0-4-nitrophenyl phosphorothioate; |
| | 0,0-diethyl-0-(2,isopropyl-6-methyl-5-pyrimidinyl) phosphorothioate; |
| | 2-diethylamino-6-methyl pyrimidine-4-yl dimethyl phosphorothioate; |
| dithiophosphates: | 0,0-dimethyl phosphorodithioate ester of diethylmercapto succinate; |
| | 0-ethyl-S-phenyl ethyl phosphorodithioate. |

Typical herbicides include phenoxy compounds, benzoic, acetic, and phthalic acids, aniline derivatives, nitriles, amides, acetamides, anilides, carbamates, thiocarbamates, and heterocyclic nitrogen derivatives, e.g., triazines, pyridines, pyridazones, picolinic acid, and urea derivates and phosphates. (See *Agricultural Chemicals*, Book II, *Herbicides*, 1986-87 Edition, W.T. Thomson, Thomson Publications, Fresno, CA 93791.) Exemplary of the above compounds are:

| | |
|---|---|
| phenoxy compounds: | 2,4-Dichlorophenoxy acetic acid |
| | 2,4,5-trichloro phenoxyacetic acid; |
| | 4-(2,4-dichlorophenoxy) butyric acid; |
| | S-ethyl 2 methyl-4-chlorophenoxy-thioacetate; |
| | 2-methyl-4-chloro-phenoxy acetic acid; |
| | methyl 5-(2,4-dichloro-phenoxy)-2-nitrobenzoate; |
| benzoic and acetic acids of phthalic compounds: | 3,6-dichloro-o-anisic acid |
| | 4-chloro-2-oxo benzothiazolin-3-yl acetic acid; |
| | N-1-Naphthyl-phthalamic acid; |
| nitriles and aniline derivatives: | 3-5-dibromo-4-hydroxybenzo-nitrile; |
| | α,α,α,trifluoro-2,6-dinitro-N,N-dipropyl-p-tolinidine; |
| | N-(1-ethylpropyl)-2,6-dinitro-3,4-xylidine; |
| amides, acetamides, anilides: | N,N-diethyl-2-(1-naphthalenyl oxy)-propionamide; |
| | 2,6-dimethyl-N-2' methoxy-ethyl-chloro-acetanilide; |
| | 3',4'-dichloro-propionanilide; |
| | α-chloracetic-N-(3,5,5-trimethyl-cyclohexen-1-yl)-N-isopropylamide; |
| | 4-benzyl-N-isopropyl trimethyl acetamide; |
| thiocarbamates: | S-ethyl dipropyl thiocarbamate; |
| urea derivatives: | 3-(5-tert-butyl-3-isoxazoyl)-1,1-dimethyl urea; |
| | N-(2,6-trifluoro-benzoyl)-N'-[2,5-dichloro-4-(1,1,2,3,3,3-hexafluoropropyloxy) phenyl] urea; |
| pyrrolidone derivatives: | 1-(m-trifluoro methyl phenyl)-3-chloro-4-chloromethyl-2-pyrrolidone; |
| amino acid derivatives: | methyl N-benzoyl-N-(3-chloro-4-fluorophenyl)-DL alarinate; |
| | N-chloroacetyl-N-(2,6-diethyl phenyl)-glycine ethyl ester; |

| | -continued |
|---|---|
| carbamates: | isopropyl-m-chlorocarbanilate; 3-ethoxy (carbonyl aminophenyl)-N-phenyl carbamate; |
| heterocyclics: | 4-amino-3,5-dichloro-6-fluoro-2-pyridyloxy acetic acid; 4-(1,2-Dimethyl-N-propyl amino)-2-ethyl amino-6-methyl thio-S-triazine; 2-[4,5-dihydro 4-methyl-4-(1-methyl ethyl)-5-oxo-1 H-imidazoyl-2yl-3-byridinecarboxylic acid; 2-[3,5-dichlorophenyl)-2-(2,2,2-trichloroethyl) oxinane; butyl-9-hydro-fluorene-(9)-carboxylate; 2-[1-(ethoxy imino) butyl]-3-hydroxy-5-(2H-tetra hydro thiopyran-3-yl)-2-cyclohexene-ione; 2-(2 chlorophenyl) methyl-4,4-dimethyl-3-iso oxazolidinone; |
| phosphates: | 0-ethyl-0-(3-methyl-6-nitro phenyl) N-sec-butyl phosphoro thio amidate. |

Typical fungicides include (See *Agricultural Chemicals*, Book IV, *Fungicides*, 1989 Revision, W.T. Thomson, Thomson Publications, Fresno, CA 93791):

| | |
|---|---|
| organic compounds: | 2,5-dimethyl-N-Cyclohexyl-N-methoxy-3-furan carboxamide; 5-Ethyoxy-3-trichloromethyl-1,2,4-thiadiazole; 3-(2-methyl piperidino) propyl 3,4-dichlorobenzoate; N,N'-(1,4-piperazinediyl bis (2,2,2-trichloro) ethylidene) bis formamide; Tetramethyl thiuram disulfide; 0-Ethyl-S,S,diphenyl-dithiophosphate; 5,10-dihydro-5,10-dioxo naphtho (2,3,9)-p-dithiin-2,3-dicarbonitrile; 2-(Thiocyano methyl thio) benzothiazole; α-2-(4-chlorophenyl) ethyl]-α-(1,1-dimethyl ethyl)-1 H-1,2,4-triazole-1-ethanol; |
| morpholines: | N-tridecyl-2,6-dimethyl morpholine; 4-N-dodecyl-2,6-dimethyl morpholine; |

Typical fumigants, growth regulators, repellants, and rodenticides include (See *Agricultural Chemicals*, Book III, *Fumigants*, 1988-1989 Revision, W.T. Thomson, Thomson Publications, Fresno, CA 93791):

| | |
|---|---|
| growth regulants: | 1,2 Dihydro-6-ethyoxy-2,2,4-trimethylquinoline; (2-chloroethyl) phosphoric acid; 4-[acetamino) methyl]-2-chloro-N (2,6-diethyl phenyl acetamide; Benzoic acid, 3,6 dichloro-2-methoxy,2-ethoxy-1-methyl-2-oxo ethyl ester; |
| repellants: | 0,0-dimethyl-0-[(4-methyl thio)-m-tolyl] phosphorothioate; Tetriary butyl-sulfenyl dimethyl dithio carbamate; |
| seed softener: | 2-chloro-6-(trichlomethyl) pyridine; 5-ethoxy-3-trichloromethyl-1,2,4-thiadiazole; N-phenyl-N'-1,2,3-thiadiazol-5-yl urea; |

Pesticides may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into two groups. The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenozy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfenamide (BETASAN ®),
Isobornyl Thiocyanoacetate (Thanite ®),
Ioxynil ester of octanoic acid,
Molinate S-ethyl hexahydro - 1 H - azepine-1-carbothioate,
PP 511 0,0-dimethyl-(2-diethylamine 4-methyl-6-pyrimidinyl) carbamate,
PP 211 0,0-diethyl O-(2-diethylamine-4-methyl-6-pyrimidinyl) phosphorocarbamate,
Chlordane
5-Ethoxy-3-(trichlorometyl)-1,2,4-thiadiazole (TERRAZALE ®),
Ethyl-s-s-dipropyl-phosphodithioate (MOCAP ®),
S-Ethyl dipropylthiocarbamate (EPTAM ®)
S-Ethyl diisobutylthiocarbamat (SUTAN ®),
S-n. propyl-di-n-propylthiocarbamate (VERNAM ®),
S-propyl butylethylthiocarbamatae (TILLAM ®),
S-ethyl ethylcyclohexylthiocarbamate (RO-NEET ®),
Malathion (S-(1,2-dicarboxyethyl)-0,0-dimethyl phosphorodithioate),
Diazinon (0,0-diethyl, 0-(2-isopropyl-4-methyl-6-pyrimidinyl) phosphorothioate,
O-Ethyl-S-phenyl-ethylphosphonodithioate (DYFONATE ®),
Toxaphene (Octachlorocamphene),
Bromoxynil (3,5-dibromo-4-hydroxy benzonitrile ester of n.octanoic acid,
2-chloro-N-2,6-diethylphenyl-N-methoxymethylacetamide (LASSO ®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.
2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5 bromo-3-sec. butyl-6-methyl uracil)
Isocil (5 bromo-3-isopropyl-6-methyl uracil)
Linuron (3-(3,4 dichlorophenyl)-1-methoxy-1 methyl urea Atrazine (2-chloro-4-ethylamino-6 isopropylamino-s-triazine) Simazine (2-chloro-4,6,-bis (ethylamino)-s-triazine)
Dodine (n-dodecylguanidine acetate)
Thiram (tetramethylthiuram disulfide)
N-(mercaptomethyl)phthalimide s-(o,o dimethylphosphorodithioate) (IMIDAN ®)
Lindane (gamma 1,2,3,4,5,6 hexachlorocyclohexane)
Folpet (N-trichloromethylphthalimide)
Manazon (s-(4,6-diamino-1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylamiline) (2,3 dihydro-5-carboxanilido-6-methyl-1,4-oxathiin) (VITAVAX ®)
2,4-dichlorophenoxyacetic acid
4-(4-chloro-2 methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Carbaryl: 1-naphthyl-N-methylcarbamate
Methoxychlor: 2,2,-Bis(p-methoxyphenyl)-1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 062: 5,6-dimethyl-2-dimethylamino-4 pyrimidinyl dimethylcarbamate*
PP 149: 5-n-butyl-2 ethylamino-4-hydroxy-6 methyl-pyrimidine*
Manufactured by Imperial Chemical Industries Limited
C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
Diphenamid NN-dimethyl-2,2-diphenylacetamide
Fenac 2,3,6-trichlorophenylacetic acid
Fluometuron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-(3H,5H)-dione
Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N'-dimethylurea
Neburon N-butyl-N'-(3,4-dichlorophenyl)-N-methylurea
NIA 11092 1,1-dimethyl-3-[3-(n-t-butyl carbamyloxy)-phenyl] urea
Mecoprop 2-(4-chloro-2 methylphenoxy)propionic acid
Monolinuron N'-(4-chlorophenyl)-N-methoxy-N-methylurea
Nitrofen 2,4-dichlorphenyl 4-nitrophenylether
Propanil N-(3,4-dichlororphenyl)propionamide
Pyriclor 2,3,5-trichloro-4-pyridinol
Solan 3'-chloro-2-methyl-p-volerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl)acetamide
Cypromid 3',4'-dichlorocyclopropane carboxanilide
Fenuron NN-dimethyl-N'phenylurea
Chlorbromuron N'-(4-bromo-3-chlorophenyl)-N-methoxy-N-methylurea
Ametryne 2-methylmercapto-4-ethylamino-6-isopropyl-amino-s-triazine
Prometryne 2-methylmercapto-4,6-bisisopropyl amino-s-triazine
DCPA dimethyl 2,3,5,6, tetrachloroterephthalate
Benefin N-butyl-N-ethyl-2,2,2-trifluoro-2,6-dinitro-p-toluidine
Nitralin 2,6-dinitro-4-methylsulfonyl-NN-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzine
1-(butile carbamoyl)-2-benzimidazol carbamic acid, methyl ester (BENLATE ®)

Examples of appropriate hydrophobic solvents include alkylpyrrolidones having an alkyl portion containing from 6 to 14 carbon atoms, e.g., octylpyrrolidone, dodecylpyrrolidone, or N-(2'-ethylhexylpyrrolidone), alkyl gammabutyrolactones, alkyl cyclic carbonates and combinations thereof, wherein the alkyl chains contain from 6 to 14 carbon atoms. The alkyl portion may be distributed at one or more sites on the ring so long as one portion contains at least 6 carbon atoms and the total number of alkyl carbon atoms does not exceed 14. Preferred 6 to 14 carbon alkyl portions are composed of straight chains. Branched or cyclic alkyl portions may also be used.

The hydrophobic solvent is preferably selected from pyrrolidones having the formula

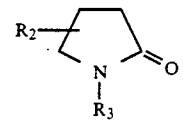

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14.

The inventive composition further comprises an organic diluent which is a synthetic or naturally occurring oil having a high hydrophobic character or having a fractional dispersive solubility parameter of greater than 70% and preferably greater than 85% and a molar volume of greater than 90 cm$^3$/mole. These properties are defined in the C.R.C. Handbook referred to hereinabove. Typical diluents include soybean oil, rapeseed oil, long chain alcohols, long chain ketones, long chain esters, and ethers. As used herein, "long chain" means with 6 or more carbon atoms. Also suitable as the organic diluent are aromatic petroleum oils including those which are commercially available distillates from crude oils having an average boiling point greater than 200° C. Typical of such materials are those sold under the trademarks Exxon 200 or Texaco 400. Of course, such aromatics should be approved for use as a carrier for agriculturally active chemicals.

The composition of the aromatic petroleum oil is generally:

Heavy aromatic solvent naphtha—about 60%;
Middle distillate solvent extractant—about 40%.

Normally, these oils contain predominantly the $C_9$-$C_{15}$ aromatic hydrocarbons and primarily the $C_{10}$-$C_{12}$ hydrocarbons having a flash point of about 203° F.

In the inventive composition, the amount of solvent is in the range from about 20 to 90%, and the amount of diluent is about 80 to 10%, based on the weight of solvent and diluent in the composition.

The inventive composition also contains one or more additional emulsifier(s) or surfactant(s) which is generally selected on a case by case basis in order to optimize the solubility and stability of the emulsion. Typically, such emulsifiers include ethoxylated alkyl phenols, linear aliphatic polyesters, linear aromatic polyesters, polyethoxylated alcohols, linear aliphatic ethoxylates, polyethoxylated castor oil, polyethoxylated carboxylates, and polyethoxylated alkylamines. Anionic surfactants may be used as the emulsifier and include phosphate esters and their salts, alkyl sulfonamides, salts of sulfated nonylphenoxypoly(ethyleneoxy) ethanol, salts of alkylbenzene sulfonates, salts of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, *Emulsifiers and Detergents* (1989), published by McCutcheon's Division of M.C. Publishing Co., Glen Rock, New Jersey.) Generally, the amount of emulsifier (surfactant) is from about 1 to 25% based on the total weight of the composition.

The agriculturally active chemical (sometimes referred to herein as AAC) concentration should be as high as possible so long as it does not precipitate out upon dilution of the concentrate with water for a reasonable period of time and achieves the desired effect. Precipitation (crystal formation) on standing not only depletes the solution of AAC, it can also lead to fouling of application equipment, i.e., sprayers, etc. With the present invention, it is possible to obtain concentrates with agriculturally active chemical concentrations in excess of 5 weight percent which form a stable emulsion upon being diluted with water. Depending on the particular agriculturally active chemical, the concentration of the AAC is from about 5 to 25% based on the total weight of the composition before dilution.

The final use concentration values depend on the AAC. However, it is important that upon dilution, the diluted form remain stable for a time sufficient to allow it to be applied. This, of course, will vary with the schedule for the application in the field. Normally, the diluted concentrate is applied within four hours of dilution. It is possible, however, due to equipment and personnel delays, that a standing period of up to 24 hours may be encountered. With the present invention, prolonged stability of the emulsified concentrate, as is, as well as in the diluted form is obtained. In particular, the emulsified concentrate in accordance with the present invention can be diluted to final use concentrations in the range from about 10 ppm to 2 percent, depending on the specific AAC, without any adverse effects, and specifically, precipitation of the AAC from the solution.

The following examples illustrate the present invention*:

In the examples, all compositional percentages are percent by weight of the total composition unless otherwise indicated.

A series of experiments was carried out wherein the type and amount of agriculturally active chemical, hydrophobic solvent, diluent, and other components were varied. The samples were evaluated for ease of emulsion and emulsion stability by measuring the amount of separation before and after mixing. The compositions used and results obtained are set forth in the tables that follow.

EXPERIMENTAL PROCEDURE

Formulations:

Formulations were prepared by weighing the exact proportion of ingredients and mixing them together in a bottle. The solvents were weighed in first. The AAC was dissolved completely in the solvent system followed by addition of the wetting agent or emulsifying agent. Typically, about 10 g of each of the formulations was prepared.

The contents were stirred well in an automatic rocking shaker for about 30 minutes when the AAC dissolved completely. The samples thus prepared were evaluated for freeze-thaw stability on storage and ease of emulsification and emulsion stability on dilution. For dilution, 2 grams of concentrate were diluted to 50 grams using World Health Organization (WHO) standard (6 g of $CaCl_2$ and 2.78 g of $MgCl_2 6H_2O$ dissolved in 20 L) hard water having a hardness of 342 ppm expressed as Na equivalent.

Freeze-Thaw Stability

The concentrates were stored for a period of 24 hours in the cold (temperature 5° C.) in a refrigerator and taken out and thawed to room temperature and then stored at 55° C. in an oven for a period of 24 hours. The alternate storage in the cold (5° C.) and warm condition at 55° C. was repeated for three cycles. Any separation during the storage was recorded. A concentrate is "stable" if there is no substantial separation after the 24 hour cycles at each temperature. All of the solutions exemplified hereinafter exhibited stability according to this test between the temperatures of 5° C. and 55° C. Some of the solutions were even stable at a lower range of −5° C.

Evaluation of Emulsion Stability and Ease of Emulsification

A Nessler tube (1.8 cm diameter; 28 cm long) was filled with an appropriate quantity (47–48 g) of WHO water. Using a serological pipette, 0.5–2.5 g of emulsion concentrate was dropped into the Nessler tube containing 47.5–49.5 g water. The initial bloom was observed at zero time without stirring and the quality of the bloom was graded by visual appearance as shown below. The Nessler tube was stopped and inverted 20 times; the bloom was again recorded and so also stability as judged by volume or height of the sedimentation (cream/ppt/oil) followed at different intervals of time: 0, 1 hour, 2 hours, up to 24 hours.

Stability of Diluted Concentrate

The composition of the concentrate (EC) diluted with water was considered "stable" if at EC concentrations of from 0.2 to 1%, the composition after mixing (twenty inversions) exhibited two mm or less cream and no oil in one hour. Both top and bottom should be checked.

| Bloom: | Excellent | Thick emulsion cloud with no separation |
|---|---|---|
| | Good | Emulsion cloud may be thin, or may exhibit trailing, small number of oil droplets within cloud |
| | Poor | Many oil droplets within cloud, some droplets separate from cloud |

Each of the emulsifiable concentrates thus prepared were analyzed for ease of emulsification (bloom) upon addition of water and after twenty inversion of the sample as well as emulsion stability upon dilution with water. The composition of the samples are set forth in Table A and the results of the analysis are set forth in Table B.

Crystal Growth on Stirring

A number of the samples were evaluated for precipitation of AAC, i.e., crystal growth over varying time periods. This was done by placing the diluted sample in a 100 ml beaker and stirring continuously. The samples were examined at 1, 4, 7, and 24 hour intervals and were examined for the presence of crystals under 200 × magnification. Samples were also tested for sediment by pouring through U.S. Standard screens (60, 100 and 250 mesh).

The components set forth in the Tables are referred to by their commercial names for purposes of brevity. The chemical nomenclature of the materials is as follows:

| | |
|---|---|
| LP-100 | N-octylpyrrolidone |
| LP-300 | N-dodecylpyrrolidone ($C_{12}$ chain) |
| LP-940 | N-octadecylpyrrolidone ($C_{18}$ chain) |
| Exxate 600 | Acetic acid ester with $C_6$-rich OXO alochol |
| Exxate 900 | Acetic acid ester with $C_9$-rich OXO alcohol |
| Exxate 1300 | Acetic acid ester with $C_{13}$-rich OXO alochol |
| Gafac RM 710 | Poly(oxy-1,2-ethanediyl)α-(dinonylphenyl)-omega-hydroxy-phosphate. |
| Igepal CO-630 | Ethoxylated nonyl phenol containing 9 EO units |
| Diuron | 3-(3,4-dichlorophenyl)-1,1-dimethylurea |
| Thidiazuron | 1-phenyl-3-(1,2,3-thiadiazol-5-yl)urea |
| Exxon 100 | Light aromatic solvent naphtha (petroleum) consists predominantly of $C_8$-$C_{10}$ aromatic hydrocarbons; boiling point range 152-168° C. |
| Exxon 150 | Heavy aromatic solvent naphtha (petroleum) consists predominantly of $C_9$-$C_{11}$ aromatic hydrocarbons; boiling point range 176-210° C. |
| Exxon 200 | Heavy aromatic solvent naphtha (petroleum) consists predominantly of $C_9$-$C_{15}$ aromatic hydrocarbons; boiling point range 217-293° C. |
| Gafac RE-610 | Poly(oxy-1,2-ethanediyl)α-(nonylphenyl)-omega-hydroxy-phosphate. |

TABLE 1-A

5% PRODIAMINE

| RUN NO. | 1 | | 2 | | 3 | | 4 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 3.68 | 92 | 3.68 | 92 | 3.68 | 92 | 1.84 | 46 |
| LP-300 | 0 | 0 | 0 | 0 | 0 | 0 | 1.84 | 46 |
| EXXON 200 | 0 | 0 | 0 | 0 | 0 | 0 | 0 | 0 |
| GAFAC RE610 | 0.12 | 3 | 0 | 0 | 0.08 | 2 | 0.12 | 3 |
| IGEPAL CO630 | 0 | 0 | 0.12 | 3 | 0.04 | 1 | 0 | 0 |
| PRODIAMINE | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |
| RESULTS: EMULSIONS: | | | | | | | | |
| 0-TIME | none | | none | | none | | none | |
| AFTER 20 TURNS | excellent | | excellent | | excellent | | excellent | |
| AFTER 24 HOURS | fair | | poor | | fair | | poor | |
| SOLIDS OR CREAMS: | SUPER | PCPT | SUPER | PCPT | SUPER | PCPT | SUPER | PCPT |
| 0-TIME NO TURNS | 10 | | 10 | | 10 | | 10 | |
| 0-TIME 20 TURNS | 0 | | 0 | | 0 | | 0 | |
| ONE HOUR | 9 | | 12 | | 9 | | 10 | |
| TWO HOURS | 9 | | 12 | | 11 | | 12 | |
| FOUR HOURS | 9 | | 12 | | 11 | | 12 | |
| 24 HOURS | 11 | | 12 | | 12 | | 12 | |

| RUN NO. | 5 | | 6 | | 7 | | 8 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 1.84 | 46 | 1.84 | 46 | 1.472 | 36.8 | 1.472 | 36.8 |
| LP-300 | 1.84 | 46 | 1.84 | 46 | 1.104 | 27.6 | 1.104 | 27.6 |
| EXXON 200 | 0 | 0 | 0 | 0 | 1.104 | 27.6 | 1.104 | 27.6 |
| GAFAC RE610 | 0 | 0 | 0.08 | 2 | 0.12 | 3 | 0 | 0 |
| IGEPAL CO630 | 0.12 | 3 | 0.04 | 1 | 0 | 0 | 0.12 | 3 |
| PRODIAMINE | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |
| RESULTS: EMULSIONS: | | | | | | | | |
| 0-TIME | none | | none | | slight | | none | |
| AFTER 20 TURNS | excellent | | excellent | | excellent | | excellent | |
| AFTER 24 HOURS | poor | | poor | | good | | poor | |
| SOLIDS OR CREAMS: | SUPER | PCPT | SUPER | PCPT | SUPER | PCPT | SUPER | PCPT |
| 0-TIME NO TURNS | 10 | | 10 | | 10 | | 10 | |
| 0-TIME 20 TURNS | 0 | | 0 | | 0 | | 0 | |

TABLE 1-A-continued

5% PRODIAMINE

|  | | | | | | | | |
|---|---|---|---|---|---|---|---|---|
| ONE HOUR | 12 | | 9 | | 0 | | 9 | |
| TWO HOURS | 12 | | 11 | | 0 | | 10 | |
| FOUR HOURS | 12 | | 11 | | 0.5 | | 10 | |
| 24 HOURS | 12 | | 12 | | 7 | | 9 | |

| RUN NO. | 9 | | 10 | | 11 | | 12 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 1.472 | 36.8 | 1.84 | 46 | 1.84 | 46 | 1.84 | 46 |
| LP-300 | 1.104 | 27.6 | 0 | 0 | 0 | 0 | 0 | 0 |
| EXXON 200 | 1.104 | 27.6 | 1.84 | 46 | 1.84 | 46 | 1.84 | 46 |
| GAFAC RE610 | 0.08 | 2 | 0.12 | 3 | 0 | 0 | 0.08 | 2 |
| IGEPAL CO630 | 0.04 | 1 | 0 | 0 | 0.12 | 3 | 0.04 | 1 |
| PRODIAMINE | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |

RESULTS:
EMULSIONS:

| | | | | | | | | |
|---|---|---|---|---|---|---|---|---|
| 0-TIME | slight | | slight | | none | | slight | |
| AFTER 20 TURNS | excellent | | excellent | | excellent | | excellent | |
| AFTER 24 HOURS | good | | excellent | | poor | | excellent | |

| SOLIDS OR CREAMS: | SUPER | PCPT | SUPER | PCPT | SUPER | PCPT | SUPER | PCPT |
|---|---|---|---|---|---|---|---|---|
| 0-TIME NO TURNS | 9 | | 4 | | 9 | | 5 | |
| 0-TIME 20 TURNS | 0 | | 0 | | 0 | | 0 | |
| ONE HOUR | 0 | | 0 | | 6 | | 0 | |
| TWO HOURS | 0.5 | | 0 | | 9 | | 0 | |
| FOUR HOURS | 1 | | 0 | | 9 | | 0 | |
| 24 HOURS | 6 | | 0.5 | | 7 | | 1 | |

| RUN NO. | 13 | | 14 | | 15 | | 16 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 0 | 0 | 0 | 0 | 0 | 0 | 0 | 0 |
| LP-300 | 1.84 | 46 | 1.84 | 46 | 1.84 | 46 | 3.68 | 92 |
| EXXON 200 | 1.84 | 46 | 1.84 | 46 | 1.84 | 46 | 0 | 0 |
| GAFAC RE610 | 0.12 | 3 | 0 | 0 | 0.08 | 2 | 0.12 | 3 |
| IGEPAL CO630 | 0 | 0 | 0.12 | 3 | 0.04 | 1 | 0 | 0 |
| PRODIAMINE | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |

RESULTS:
EMULSIONS:

| | | | | | | | | |
|---|---|---|---|---|---|---|---|---|
| 0-TIME | slight | | slight | | slight | | none | |
| AFTER 20 TURNS | excellent | | excellent | | excellent | | excellent | |
| AFTER 24 HOURS | excellent | | poor | | excellent | | very poor | |

| SOLIDS OR CREAMS: | SUPER | PCPT | SUPER | PCPT | SUPER | PCPT | SUPER | PCPT |
|---|---|---|---|---|---|---|---|---|
| 0-TIME NO TURNS | 6 | | 6 | | 5 | | 9 | |
| 0-TIME 20 TURNS | 0 | | 0 | | 0 | | 0 | |
| ONE HOUR | 0 | | 7 | | 0 | | 16 | |
| TWO HOURS | 0 | | 8 | | 0 | | 16 | |
| FOUR HOURS | 0 | | 9 | | 0 | | 16 | |
| 24 HOURS | 0 | | 9 | | 0 | | 16 | |

| RUN NO. | 17 | | 18 | |
|---|---|---|---|---|
| COMPOSITION WT. % | DILUTED* | CONC. | DILUTED* | CONC. |
| LP-100 | 0 | 0 | 0 | 0 |
| LP-300 | 3.68 | 92 | 3.68 | 92 |
| EXXON 200 | 0 | 0 | 0 | 0 |
| GAFAC RE610 | 0 | 0 | 0.08 | 2 |
| IGEPAL CO630 | 0.12 | 3 | 0.04 | 1 |
| PRODIAMINE | 0.2 | 5 | 0.2 | 5 |
| HARD WATER | 96 | 0 | 96 | 0 |
| TOTAL | 100 | 100 | 100 | 100 |

RESULTS:
EMULSIONS:

| | | | | |
|---|---|---|---|---|
| 0-TIME | none | | none | |
| AFTER 20 TURNS | excellent | | excellent | |
| AFTER 24 HOURS | none | | very poor | |

| SOLIDS OR CREAMS: | SUPER | PCPT | SUPER | PCPT |
|---|---|---|---|---|
| 0-TIME NO TURNS | 9 | | 9 | |
| 0-TIME 20 TURNS | 0 | | 0 | |
| ONE HOUR | 12 | | 15 | |
| TWO HOURS | 12 | | 16 | |
| FOUR HOURS | 13 | | 16 | |

TABLE 1-A-continued

| 5% PRODIAMINE | | |
|---|---|---|
| 24 HOURS | 15 | 16 |

*Diluted 2 to 50 grams. 10% runs were performed on selected blends and depicted in Table 1-B.

TABLE 1-B

10% PRODIAMINE

| RUN NO. | 19 | | 20 | | 21 | |
|---|---|---|---|---|---|---|
| COMPOSITION WT. % | DILUTED* | CONC. | DILUTED* | CONC. | DILUTED* | CONC. |
| LP-100 | 0.85 | 42.5 | 0.85 | 42.5 | 0.85 | 42.5 |
| LP-300 | 0.85 | 42.5 | 0 | 0 | 0 | 0 |
| EXXON 200 | 0 | 0 | 0.85 | 42.5 | 0.85 | 42.5 |
| GAFAC RE610 | 0.1 | 5 | 0.1 | 5 | 0.06 | 3 |
| IGEPAL CO630 | 0 | 0 | 0 | 0 | 0.04 | 2 |
| PRODIAMINE | 0.2 | 10 | 0.2 | 10 | 0.2 | 10 |
| HARD WATER | 98 | 0 | 98 | 0 | 98 | 0 |
| TOTAL | 100 | 100 | 100 | 100 | 100 | 100 |

RESULTS:
EMULSIONS:

| | | | | | | |
|---|---|---|---|---|---|---|
| 0-TIME | none | | fair | | poor | |
| AFTER 20 TURNS | excellent | | excellent | | excellent | |
| AFTER 24 HOURS | poor | | excellent | | excellent | |

| SOLIDS OR CREAMS: | SUPER | PCPT | SUPER | PCPT | SUPER | PCPT |
|---|---|---|---|---|---|---|
| 0-TIME NO TURNS | 4 | 0 | 3 | 0 | 3 | 0 |
| 0-TIME 20 TURNS | 0 | 0 | 0 | 0 | 0 | 0 |
| ONE HOUR | 4 | 0 | 0 | 0 | 0 | 0 |
| TWO HOURS | 4 | 0 | 0 | 0 | 0 | 0 |
| FOUR HOURS | 4 | 0 | 0 | 0 | 0 | 0 |
| 24 HOURS | 10 | 0 | 1 | 0 | 1 | 0 |

| RUN NO. | 22 | | 23 | |
|---|---|---|---|---|
| COMPOSITION WT. % | DILUTED* | CONC. | DILUTED* | CONC. |
| LP-100 | 0 | 0 | 0 | 0 |
| LP-300 | 0.85 | 42.5 | 0.85 | 42.5 |
| EXXON 200 | 0.85 | 42.5 | 0.85 | 42.5 |
| GAFAC RE610 | 0.1 | 5 | 0.06 | 3 |
| IGEPAL CO630 | 0 | 0 | 0.04 | 2 |
| PRODIAMINE | 0.2 | 10 | 0.2 | 10 |
| HARD WATER | 98 | 0 | 98 | 0 |
| TOTAL | 100 | 100 | 100 | 100 |

RESULTS:
EMULSIONS:

| | | | | |
|---|---|---|---|---|
| 0-TIME | poor | | poor | |
| AFTER 20 TURNS | excellent | | excellent | |
| AFTER 24 HOURS | excellent | | excellent | |

| SOLIDS OR CREAMS: | SUPER | PCPT | SUPER | PCPT |
|---|---|---|---|---|
| 0-TIME NO TURNS | 3 | 0 | 3 | 0 |
| 0-TIME 20 TURNS | 0 | 0 | 0 | 0 |
| ONE HOUR | 0 | 0 | 0 | 0 |
| TWO HOURS | 0 | 0 | 0 | 0 |
| FOUR HOURS | 0 | 0 | 0 | 0 |
| 24 HOURS | 0.5 | 0 | 0.5 | 0 |

*Diluted 1 to 50 grams. 20% runs were performed on selected blends and depicted in Table 1-C.

TABLE 1-C

20% PRODIAMINE

| RUN NO. | 24 | | 25 | | 26 | | 27 | |
|---|---|---|---|---|---|---|---|---|
| COMPONENT | DILUTED* | CONC. | DILUTED* | CONC. | DILUTED* | CONC. | DILUTED* | CONC. |
| LP-100 | 0.375 | 37.5 | 0.375 | 37.5 | 0 | 0 | 0 | 0 |
| LP-300 | 0 | 0 | 0 | 0 | 0.375 | 37.5 | 0.375 | 37.5 |
| EXXON 200 | 0.375 | 37.5 | 0.375 | 37.5 | 0.375 | 37.5 | 0.375 | 37.5 |
| GAFAC RE610 | 0.5 | 5 | 0.03 | 2 | 0.05 | 5 | 0.03 | 3 |
| IGEPAL CO630 | 0 | 0 | 0.02 | 2 | 0 | 0 | 0.02 | 2 |
| PRODIAMINE | 0.2 | 20 | 0.2 | 20 | 0.2 | 20 | 0.2 | 20 |
| HARD WATER | 99 | 0 | 99 | 0 | 99 | 0 | 99 | 0 |
| TOTAL | 100 | 100 | 100 | 100 | 100 | 100 | 100 | 100 |

RESULTS:
EMULSIONS:

| | | | | |
|---|---|---|---|---|
| 0-TIME | poor | poor | poor | very poor |
| AFTER 20 TURNS | excellent | excellent | excellent | excellent |
| AFTER 24 HOURS | excellent | excellent | excellent | excellent |

TABLE 1-C-continued

| | 20% PRODIAMINE | | | | | | | |
|---|---|---|---|---|---|---|---|---|
| SOLIDS OR CREAMS: | SUPER | PCPT | SUPER | PCPT | SUPER | PCPT | SUPER | PCPT |
| 0-TIME NO TURNS | 0 | 2 | 0 | 2 | 0 | 2 | 0 | 2 |
| 0-TIME 20 TURNS | 0 | 0 | 0 | 0 | 0 | 0 | 0 | 0 |
| ONE HOUR | 0 | 0 | 0 | 0 | 0 | 0 | 0 | 0 |
| TWO HOURS | 0 | 0.5 | 0 | 0.5 | 0 | 0.5 | 0 | 0.5 |
| FOUR HOURS | 0 | 1 | 0 | 1 | 0 | 1 | 0 | 1 |
| 24 HOURS | 0 | 1 | 0 | 1 | 0 | 1 | 0 | 1 |

*Diluted 0.5 to 50 grams. Isooctyl pyrrolidone runs were performed on selected blends and depicted in Table 1-D.

TABLE 1-D

| | 20% PRODIAMINE | | | |
|---|---|---|---|---|
| RUN NO. | 28 | | 29 | |
| COMPOSITION WT. % | DILUTED* | CONC. | DILUTED* | CONC. |
| ISOOCTYL PYROL | 0.375 | 37.5 | 0.375 | 37.5 |
| LP-300 | 0 | 0 | 0 | 0 |
| EXXON 200 | 0.375 | 37.5 | 0.375 | 37.5 |
| GAFAC RE610 | 0.05 | 5 | 0.03 | 3 |
| IGEPAL CO630 | 0 | 0 | 0.02 | 2 |
| PRODIAMINE | 0.2 | 20 | 0.2 | 20 |
| HARD WATER | 99 | 0 | 99 | 0 |
| TOTAL | 100 | 100 | 100 | 100 |
| RESULTS: | | | | |
| EMULSIONS: | | | | |
| 0-TIME | very poor | | very poor | |
| AFTER 20 TURNS | excellent | | excellent | |
| AFTER 24 HOURS | excellent | | excellent | |
| SOLIDS OR CREAMS: | SUPER | PCPT | SUPER | PCPT |
| 0-TIME NO TURNS | 0 | 2 | 0 | 2 |
| 0-TIME 20 TURNS | 0 | 0 | 0 | 0 |
| ONE HOUR | 0 | 0.5 | 0 | 0.5 |
| TWO HOURS | 0 | 1 | 0 | 1 |
| FOUR HOURS | 0 | 2 | 0 | 2 |
| 24 HOURS | 0 | 5 | 0 | 5 |

*Diluted 0.5 grams to 50.

TABLE 2-A

| | 5% CGA | | | | | | | |
|---|---|---|---|---|---|---|---|---|
| RUN NO. | 30 | | 31 | | 32 | | 33 | |
| COMPOSITION WT. % | DILUTED | CONC. | DILUTED* | CONC. | DILUTED* | CONC. | DILUTED* | CONC. |
| LP-100 | 3.68 | 92 | 3.68 | 92 | 3.68 | 92 | 1.84 | 46 |
| LP-300 | 0 | 0 | 0 | 0 | 0 | 0 | 1.84 | 46 |
| EXXON 200 | 0 | 0 | 0 | 0 | 0 | 0 | 0 | 0 |
| GAFAC RE610 | 0.12 | 3 | 0 | 0 | 0.08 | 2 | 0.12 | 3 |
| IGEPAL CO630 | 0 | 0 | 0.12 | 3 | 0.04 | 1 | 0 | 0 |
| CGA 184699 | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |
| RESULTS: | | | | | | | | |
| EMULSIONS: | | | | | | | | |
| 0-TIME | none | | none | | none | | none | |
| AFTER 20 TURNS | excellent | | excellent | | excellent | | excellent | |
| AFTER 24 HOURS | fair | | poor | | fair | | none | |
| SOLIDS OR CREAMS: | SUPER | PCPT | SUPER | PCPT | SUPER | PCPT | SUPER | PCPT |
| 0-TIME NO TURNS | 10 | | 10 | | 10 | | 10 | |
| 0-TIME 20 TURNS | 0 | | 0 | | 0 | | 0 | |
| ONE HOUR | 6 | 12 | | 8 | | 12 | | |
| TWO HOURS | 9 | 14 | | 10 | | 12 | | |
| FOUR HOURS | 10 | 14 | | 10 | | 13 | | |
| 24 HOURS | 10 | 14 | | 10 | | 14 | | |

| RUN NO. | 34 | | 35 | | 36 | | 37 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 1.84 | 46 | 1.84 | 46 | 1.472 | 36.8 | 1.472 | 36.8 |
| LP-300 | 1.84 | 46 | 1.84 | 46 | 1.104 | 27.6 | 1.104 | 27.6 |
| EXXON 200 | 0 | 0 | 0 | 0 | 1.104 | 27.6 | 1.104 | 27.6 |
| GAFAC RE610 | 0 | 0 | 0.08 | 2 | 0.12 | 3 | 0 | 0 |
| IGEPAL CO630 | 0.12 | 3 | 0.04 | 1 | 0 | 0 | 0.12 | 3 |
| CGA 184699 | 0.2 | 5 | 0.2 | 5 | 0.2 | 5 | 0.2 | 5 |
| HARD WATER | 96 | 0 | 96 | 0 | 96 | 0 | 96 | 0 |

TABLE 2-A-continued

5% CGA

| TOTAL | 100 | 100 | 100 | 100 | 100 | 100 | 100 | 100 |
|---|---|---|---|---|---|---|---|---|
| RESULTS: EMULSIONS: | | | | | | | | |
| 0-TIME | none | | none | | none | | none | |
| AFTER 20 TURNS | excellent | | excellent | | excellent | | excellent | |
| AFTER 24 HOURS | none | | none | | fair | | poor | |
| SOLIDS OR CREAMS: | SUPER | PCPT | SUPER | PCPT | SUPER | PCPT | SUPER | PCPT |
| 0-TIME NO TURNS | 10 | | 10 | | 10 | | 10 | |
| 0-TIME 20 TURNS | 0 | | 0 | | 0 | | 0 | |
| ONE HOUR | 11 | | 11 | | 0 | | 9 | |
| TWO HOURS | 12 | | 12 | | 0 | | 11 | |
| FOUR HOURS | 12 | | 12 | | 1 | | 11 | |
| 24 HOURS | 14 | | 12 | | 5 | | 11 | |

| RUN NO. | 38 | | 39 | | 40 | | 41 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 1.472 | 36.8 | 1.84 | 46 | 1.84 | 46 | 1.84 | 46 |
| LP-300 | 1.104 | 27.6 | 0 | 0 | 0 | 0 | 0 | 0 |
| EXXON 200 | 1.104 | 27.6 | 1.84 | 46 | 1.84 | 46 | 1.84 | 46 |
| GAFAC RE610 | 0.08 | 2 | 0.12 | 3 | 0 | 0 | 0.08 | 2 |
| IGEPAL CO630 | 0.04 | 1 | 0 | 0 | 0.12 | 3 | 0.04 | 1 |
| CGA 184699 | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |
| RESULTS: EMULSIONS: | | | | | | | | |
| 0-TIME | slight | | poor | | none | | slight | |
| AFTER 20 TURNS | excellent | | excellent | | excellent | | excellent | |
| AFTER 24 HOURS | fair | | fair | | good | | excellent | |
| SOLIDS OR CREAMS: | SUPER | PCPT | SUPER | PCPT | SUPER | PCPT | SUPER | PCPT |
| 0-TIME NO TURNS | 8 | | 3 | | 10 | | 3 | |
| 0-TIME 20 TURNS | 0 | | 0 | | 0 | | 0 | |
| ONE HOUR | 0 | | 0 | | 0 | | 0 | |
| TWO HOURS | 0 | | 0 | | 0 | | 0 | |
| FOUR HOURS | 1 | | 0 | | 0 | | 0 | |
| 24 HOURS | 5 | | 1 | | 2 | | 2 | |

| RUN NO. | 42 | | 43 | | 44 | | 45 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 0 | 0 | 0 | 0 | 0 | 0 | 0 | 0 |
| LP-300 | 1.84 | 46 | 1.84 | 46 | 1.84 | 46 | 3.68 | 92 |
| EXXON 200 | 1.84 | 46 | 1.84 | 46 | 1.84 | 46 | 0 | 0 |
| GAFAC RE610 | 0.12 | 3 | 0 | 0 | 0.08 | 2 | 0.12 | 3 |
| IGEPAL CO630 | 0 | 0 | 0.12 | 3 | 0.04 | 1 | 0 | 0 |
| CGA 184699 | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |
| RESULTS: EMULSIONS: | | | | | | | | |
| 0-TIME | slight | | slight | | slight | | none | |
| AFTER 20 TURNS | excellent | | excellent | | excellent | | fair | |
| AFTER 24 HOURS | excellent | | fair | | excellent | | none | |
| SOLIDS OR CREAMS: | SUPER | PCPT | SUPER | PCPT | SUPER | PCPT | SUPER | PCPT |
| 0-TIME NO TURNS | 5 | | 2 | | 5 | | 10 | |
| 0-TIME 20 TURNS | 0 | | 0 | | 0 | | 0 | |
| ONE HOUR | 0 | | 6 | | 0 | | 15 | |
| TWO HOURS | 0 | | 9 | | 0 | | 20 | |
| FOUR HOURS | 1 | | 9 | | 0 | | 20 | |
| 24 HOURS | 1 | | 10 | | 0 | | 20 | |

| RUN NO. | 46 | | 47 | |
|---|---|---|---|---|
| COMPOSITION WT. % | DILUTED* | CONC. | DILUTED* | CONC. |
| LP-100 | 0 | 0 | 0 | 0 |
| LP-300 | 3.68 | 92 | 3.68 | 92 |
| EXXON 200 | 0 | 0 | 0 | 0 |
| GAFAC RE610 | 0 | 0 | 0.08 | 2 |
| IGEPAL CO630 | 0.12 | 3 | 0.04 | 1 |
| CGA 185699 | 0.2 | 5 | 0.2 | 5 |
| HARD WATER | 96 | 0 | 96 | 0 |
| TOTAL | 100 | 100 | 100 | 100 |
| RESULTS: EMULSIONS: | | | | |
| 0-TIME | none | | none | |

TABLE 2-A-continued

| 5% CGA | | | | | |
|---|---|---|---|---|---|
| AFTER 20 TURNS | | fair | | fair | |
| AFTER 24 HOURS | | none | | none | |
| SOLIDS OR CREAMS: | | SUPER | PCPT | SUPER | PCPT |
| 0-TIME NO TURNS | | 10 | | 10 | |
| 0-TIME 20 TURNS | | 0 | | 0 | |
| ONE HOUR | | 15 | | 16 | |
| TWO HOURS | | 15 | | 17 | |
| FOUR HOURS | | 15 | | 17 | |
| 24 HOURS | | 16 | | 19 | |

*Diluted 2 to 50 grams. 10% runs were performed on selected blends and depicted in Table 2-B.

TABLE 2-B

| 10% CGA | | | | | | |
|---|---|---|---|---|---|---|
| RUN NO. | 48 | | 49 | | 50 | |
| COMPOSITION WT. % | DILUTED* | CONC. | DILUTED* | CONC. | DILUTED* | CONC. |
| LP-100 | 0.85 | 42.5 | 0.85 | 42.5 | 0.85 | 42.5 |
| LP-300 | 0.85 | 42.5 | 0 | 0 | 0 | 0 |
| EXXON 200 | 0 | 0 | 0.85 | 42.5 | 0.85 | 42.5 |
| GAFAC RE610 | 0.1 | 5 | 0.1 | 5 | 0.06 | 3 |
| IGEPAL CO630 | 0 | 0 | 0 | 0 | 0.04 | 2 |
| CGA 184699 | 0.2 | 10 | 0.2 | 10 | 0.2 | 10 |
| HARD WATER | 98 | 0 | 98 | 0 | 98 | 0 |
| TOTAL | 100 | 100 | 100 | 100 | 100 | 100 |

RESULTS:
EMULSIONS:

| | | | | | | |
|---|---|---|---|---|---|---|
| 0-TIME | none | | fair | | fair | |
| AFTER 20 TURNS | excellent | | excellent | | excellent | |
| AFTER 24 HOURS | none | | excellent | | excellent | |
| SOLIDS OR CREAMS: | SUPER | PCPT | SUPER | PCPT | SUPER | PCPT |
| 0-TIME NO TURNS | 4 | 0 | 0 | 0.5 | 0 | 1 |
| 0-TIME 20 TURNS | 0 | 0 | 0 | 0 | 0 | 0 |
| ONE HOUR | 3 | 0 | 0 | 0 | 0 | 0 |
| TWO HOURS | 4 | 0 | 0 | 0 | 0 | 0 |
| FOUR HOURS | 4 | 0 | 0 | 0 | 0 | 0 |
| 24 HOURS | 10 | 0 | 0 | 5 | 0 | 5 |

| RUN NO. | 51 | | 52 | |
|---|---|---|---|---|
| COMPOSITION WT. % | DILUTED* | CONC. | DILUTED* | CONC. |
| LP-100 | 0 | 0 | 0 | 0 |
| LP-300 | 0.85 | 42.5 | 0.85 | 42.5 |
| EXXON 200 | 0.85 | 42.5 | 0.85 | 42.5 |
| GAFAC RE610 | 0.1 | 5 | 0.06 | 3 |
| IGEPAL CO630 | 0 | 0 | 0.04 | 2 |
| CGA 184699 | 0.2 | 10 | 0.2 | 10 |
| HARD WATER | 98 | 0 | 98 | 0 |
| TOTAL | 100 | 100 | 100 | 100 |

RESULTS:
EMULSIONS:

| | | | | |
|---|---|---|---|---|
| 0-TIME | poor | | poor | |
| AFTER 20 TURNS | excellent | | excellent | |
| AFTER 24 HOURS | excellent | | excellent | |
| SOLIDS OR CREAMS: | SUPER | PCPT | SUPER | PCPT |
| 0-TIME NO TURNS | 0 | 0.5 | 0 | 0.5 |
| 0-TIME 20 TURNS | 0 | 0 | 0 | 0 |
| ONE HOUR | 0 | 0 | 0 | 0 |
| TWO HOURS | 0 | 0 | 0 | 0 |
| FOUR HOURS | 0 | 0 | 0 | 0 |
| 24 HOURS | 4 | 0 | 0 | 1 |

*Diluted 1 to 50 grams. 20% runs were performed on selected blends and depicted in Table 2-C.

TABLE 2-C

| 20% CGA | | | | | | | | |
|---|---|---|---|---|---|---|---|---|
| RUN NO. | 53** | | 54** | | 55** | | 56** | |
| COMPOSITION WT. % | DILUTED | CONC. | DILUTED* | CONC. | DILUTED* | CONC. | DILUTED* | CONC. |
| LP-100 | 0.375 | 37.5 | 0.375 | 37.5 | 0 | 0 | 0 | 0 |
| LP-300 | 0 | 0 | 0 | 0 | 0.375 | 37.5 | 0.375 | 37.5 |
| EXXON 200 | 0.375 | 37.5 | 0.375 | 37.5 | 0.375 | 37.5 | 0.375 | 37.5 |
| GAFAC RE610 | 0.05 | 5 | 0.03 | 3 | 0.05 | 5 | 0.03 | 3 |
| IGEPAL CO630 | 0 | 0 | 0.02 | 2 | 0 | 0 | 0.02 | 2 |

TABLE 2-C-continued

| | 20% CGA | | | | | | | |
|---|---|---|---|---|---|---|---|---|
| CGA 184699 | 0.2 | 20 | 0.2 | 20 | 0.2 | 20 | 0.2 | 20 |
| HARD WATER | 99 | 0 | 99 | 0 | 99 | 0 | 99 | 0 |
| TOTAL | 100 | 100 | 100 | 100 | 100 | 100 | 100 | 100 |
| RESULTS: EMULSIONS: | | | | | | | | |
| 0-TIME | very poor | | very poor | | poor | | very poor | |
| AFTER 20 TURNS | excellent | | excellent | | excellent | | excellent | |
| AFTER 24 HOURS | excellent | | excellent | | excellent | | excellent | |
| SOLIDS OR CREAMS: | SUPER | PCPT | SUPER | PCPT | SUPER | PCPT | SUPER | PCPT |
| 0-TIME NO TURNS | 0 | 2 | 0 | 2 | 0 | 2 | 0 | 2 |
| 0-TIME 20 TURNS | 0 | 0 | 0 | 0 | 0 | 0 | 0 | 0 |
| ONE HOUR | 0 | 0 | 0 | 0 | 0 | 0 | 0 | 0 |
| TWO HOURS | 0 | 0 | 0 | 0 | 0 | 0 | 0 | 0 |
| FOUR HOURS | 0 | 1 | 0 | 1 | 0 | 1 | 0 | 1 |
| 24 HOURS | 0 | 5 | 0 | 4 | 0 | 3 | 0 | 1 |

*Diluted 0.5 to 50 grams. Isooctyl pyrrolidone runs performed on selected blends and depicted in Table 2-D.
**2 g of the concentrates were added to 48 g standard $H_2O$. After 0, 2.0 and 24 hours of continuous stirring, no crystal formation was observed under 200 x.

TABLE 2-D

| | 20% CGA ISO | | | |
|---|---|---|---|---|
| RUN NO. | 57 | | 58 | |
| COMPOSITION WT. % | DILUTED* | CONC. | DILUTED* | CONC. |
| ISOOCTYL PYROL | 0.375 | 37.5 | 0.375 | 37.5 |
| LP-300 | 0 | 0 | 0 | 0 |
| EXXON 200 | 0.375 | 37.5 | 0.375 | 37.5 |
| GAFAC RE610 | 0.05 | 5 | 0.03 | 3 |
| IGEPAL CO630 | 0 | 0 | 0.02 | 2 |
| CGA 184699 | 0.2 | 20 | 0.2 | 20 |
| HARD WATER | 99 | 0 | 99 | 0 |
| TOTAL | 100 | 100 | 100 | 100 |
| RESULTS: EMULSIONS: | | | | |
| 0-TIME | none | | none | |
| AFTER 20 TURNS | excellent | | excellent | |
| AFTER 24 HOURS | excellent | | good | |
| SOLIDS OR CREAMS: | SUPER | PCPT | SUPER | PCPT |
| 0-TIME NO TURNS | 0 | 2 | 0 | 2 |
| 0-TIME 20 TURNS | 0 | 0 | 0 | 0 |
| ONE HOUR | 0 | 0.5 | 0 | 0.5 |
| TWO HOURS | 0 | 1 | 0 | 1 |
| FOUR HOURS | 0 | 2 | 0 | 2 |
| 24 HOURS | 0 | 4 | 0 | 5 |

*Diluted 0.5 grams to 50.

TABLE 2-E

| | 20% CGA 10% SURFACTANT | | | | | |
|---|---|---|---|---|---|---|
| RUN NO. | 59 | | 60 | | 61 | |
| COMPOSITION WT. % | DILUTED* | CONC. | DILUTED* | CONC. | DILUTED* | CONC. |
| LF-100 | 0.35 | 35 | 0.35 | 35 | 0 | 0 |
| LP-300 | 0 | 0 | 0 | 0 | 0.35 | 35 |
| EXXON 200 | 0.35 | 35 | 0.35 | 35 | 0.35 | 35 |
| GAFAC RE610 | 0.1 | 10 | 0.05 | 5 | 0.1 | 10 |
| IGEPAL CO630 | 0 | 0 | 0.05 | 5 | 0 | 0 |
| ACTIVE | 0.2 | 20 | 0.2 | 20 | 0.2 | 20 |
| HARD WATER | 99 | 0 | 99 | 0 | 99 | 0 |
| TOTAL | 100 | 100 | 100 | 100 | 100 | 100 |
| RESULTS: EMULSIONS: | | | | | | |
| 0-TIME | fair | | fair | | good | |
| AFTER 20 TURNS | excellent | | excellent | | excellent | |
| AFTER 24 HOURS | excellent | | excellent | | excellent | |
| SOLIDS OR CREAMS: | SUPER | PCPT | SUPER | PCPT | SUPER | PCPT |
| 0-TIME NO TURNS | 0 | 1 | 0 | 1 | 0 | 0.5 |
| 0-TIME 20 TURNS | 0 | 0 | 0 | 0 | 0 | 0 |
| ONE HOUR | 0 | 0 | 0 | 0 | 0 | 0 |
| TWO HOURS | 0 | 0.5 | 0 | 0.5 | 0 | 0.5 |
| FOUR HOURS | 0 | 0.5 | 0 | 1 | 0 | 1 |
| 24 HOURS | 0 | 2 | 0 | 4 | 0 | 3 |

TABLE 2-E-continued

20% CGA 10% SURFACTANT

| RUN NO. | 62 | | 63 | |
|---|---|---|---|---|
| COMPOSITION WT. % | DILUTED* | CONC. | DILUTED* | CONC. |
| LP-100 | 0 | 0 | 0.175 | 17.5 |
| LP-300 | 0.35 | 35 | 0.175 | 17.5 |
| EXXON 200 | 0.35 | 35 | 0.35 | 35 |
| GAFAC RE610 | 0.05 | 5 | 0.05 | 5 |
| IGEPAL CO630 | 0.05 | 5 | 0.05 | 5 |
| ACTIVE | 0.2 | 20 | 0.2 | 20 |
| HARD WATER | 99 | 0 | 99 | 0 |
| TOTAL | 100 | 100 | 100 | 100 |
| RESULTS: EMULSIONS: | | | | |
| 0-TIME | fair | | fair | |
| AFTER 20 TURNS | excellent | | excellent | |
| AFTER 24 HOURS | excellent | | excellent | |
| SOLIDS OR CREAMS: | SUPER | PCPT | SUPER | PCPT |
| 0-TIME NO TURNS | 0 | 1 | 0 | 1 |
| 0-TIME 20 TURNS | 0 | 0 | 0 | 0 |
| ONE HOUR | 0 | 0 | 0 | 0 |
| TWO HOURS | 0 | 0.5 | 0 | 0.5 |
| FOUR HOURS | 0 | 1 | 0 | 1 |
| 24 HOURS | 0 | 2 | 0 | 2 |

*Diluted 1 to 50 grams.

TABLE 3-A

5% PROWL

| RUN NO. | 64 | | 65 | | 66 | | 67 | |
|---|---|---|---|---|---|---|---|---|
| COMPOSITION WT. % | DILUTION* | CONC. | DILUTION* | CONC. | DILUTION* | CONC. | DILUTION* | CONC. |
| LP-100 | 3.68 | 92 | 3.68 | 92 | 3.68 | 92 | 1.84 | 46 |
| LP-300 | 0 | 0 | 0 | 0 | 0 | 0 | 1.84 | 46 |
| EXXON 200 | 0 | 0 | 0 | 0 | 0 | 0 | 0 | 0 |
| GAFAC RE610 | 0.12 | 3 | 0 | 0 | 0.08 | 2 | 0.12 | 3 |
| IGEPAL CO630 | 0 | 0 | 0.12 | 3 | 0.04 | 1 | 0 | 0 |
| PROWL | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |
| RESULTS: EMULSIONS: | | | | | | | | |
| 0-TIME | poor | | poor | | poor | | poor | |
| AFTER 20 TURNS | excellent | | good | | excellent | | excellent | |
| AFTER 24 HOURS | good | | poor | | good | | poor | |
| SOLIDS OR CREAMS: | SUPER | PCPT | SUPER | PCPT | SUPER | PCPT | SUPER | PCPT |
| 0-TIME NO TURNS | 11 | | 12 | | 10 | | 11 | |
| 0-TIME 20 TURNS | 1 | | 11 | | 1 | | 6 | |
| ONE HOUR | 5 | | 13 | | 5 | | 7 | |
| TWO HOURS | 7 | | 14 | | 8 | | 11 | |
| FOUR HOURS | 10 | | 15 | | 10 | | 14 | |
| 24 HOURS | 13 | | 15 | | 13 | | 15 | |

| RUN NO. | 68 | | 69 | | 70 | | 71 | |
|---|---|---|---|---|---|---|---|---|
| COMPOSITION WT. % | DILUTION* | CONC. | DILUTION* | CONC. | DILUTION* | CONC. | DILUTION* | CONC. |
| LP-100 | 1.84 | 46 | 1.84 | 46 | 1.472 | 36.8 | 1.472 | 36.8 |
| LP-300 | 1.84 | 46 | 1.84 | 46 | 1.104 | 27.6 | 1.104 | 27.6 |
| EXXON 200 | 0 | 0 | 0 | 0 | 1.104 | 27.6 | 1.104 | 27.6 |
| GAFAC RE610 | 0 | 0 | 0.08 | 2 | 0.12 | 3 | 0 | 0 |
| IGEPAL CO630 | 0.12 | 3 | 0.04 | 1 | 0 | 0 | 0.12 | 3 |
| PROWL | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |
| RESULTS: EMULSIONS: | | | | | | | | |
| 0-TIME | poor | | poor | | poor | | poor | |
| AFTER 20 TURNS | good | | excellent | | excellent | | good | |
| AFTER 24 HOURS | poor | | poor | | good | | fair | |
| SOLIDS OR CREAMS: | SUPER | PCPT | SUPER | PCPT | SUPER | PCPT | SUPER | PCPT |
| 0-TIME NO TURNS | 11 | | 11 | | 62 | | 10 | |
| 0-TIME 20 TURNS | 11 | | 1 | | 0 | | 4 | |
| ONE HOUR | 12 | | 8 | | 0 | | 7 | |
| TWO HOURS | 12 | | 11 | | 0 | | 9 | |
| FOUR HOURS | 13 | | 11 | | 1 | | 10 | |

TABLE 3-A-continued

5% PROWL

| 24 HOURS | 14 | | 14 | | 7 | | 11 | |
|---|---|---|---|---|---|---|---|---|
| RUN NO. | 72 | | 73 | | 74 | | 75 | |
| COMPOSITION WT. % | DILUTION* | CONC. | DILUTION* | CONC. | DILUTION* | CONC. | DILUTION* | CONC. |
| LP-100 | 1.472 | 36.8 | 1.84 | 46 | 1.84 | 46 | 1.84 | 46 |
| LP-300 | 1.104 | 27.6 | 0 | 0 | 0 | 0 | 0 | 0 |
| EXXON 200 | 1.104 | 27.6 | 1.84 | 46 | 1.84 | 46 | 1.84 | 46 |
| GAFAC RE610 | 0.08 | 2 | 0.12 | 3 | 0 | 0 | 0.08 | 2 |
| IGEPAL CO630 | 0.04 | 1 | 0 | 0 | 0.12 | 3 | 0.04 | 1 |
| PROWL | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |

RESULTS:
EMULSIONS:

| 0-TIME | poor | | poor | | poor | | poor | |
|---|---|---|---|---|---|---|---|---|
| AFTER 20 TURNS | excellent | | excellent | | excellent | | excellent | |
| AFTER 24 HOURS | good | | excellent | | fair | | good | |
| SOLIDS OR CREAMS: | SUPER | PCPT | SUPER | PCPT | SUPER | PCPT | SUPER | PCPT |
| 0-TIME NO TURNS | 34 | | 12 | | 10 | | 55 | |
| 0-TIME 20 TURNS | 1 | | 0 | | 1 | | 0 | |
| ONE HOUR | 1 | | 0 | | 3 | | 0 | |
| TWO HOURS | 1 | | 0 | | 7 | | 0 | |
| FOUR HOURS | 2 | | 0 | | 8 | | 0.5 | |
| 24 HOURS | 7 | | 3 | | 10 | | 5 | |

| RUN NO. | 76 | | 77 | | 78 | | 79 | |
|---|---|---|---|---|---|---|---|---|
| COMPOSITION WT. % | DILUTION* | CONC. | DILUTION* | CONC. | DILUTION* | CONC. | DILUTION* | CONC. |
| LP-100 | 0 | 0 | 0 | 0 | 0 | 0 | 0 | 0 |
| LP-300 | 1.84 | 46 | 1.84 | 46 | 1.84 | 46 | 3.68 | 92 |
| EXXON 200 | 1.84 | 46 | 1.84 | 46 | 1.84 | 46 | 0 | 0 |
| GAFAC RE610 | 0.12 | 3 | 0 | 0 | 0.08 | 2 | 0.12 | 3 |
| IGEPAL CO630 | 0 | 0 | 0.12 | 3 | 0.04 | 1 | 0 | 0 |
| PROWL | 0.2 | 5 | 0.2 | 5 | 0.2 | 5 | 0.2 | 5 |
| HARD WATER | 96 | 0 | 96 | 0 | 96 | 0 | 96 | 0 |
| TOTAL | 100 | 100 | 100 | 100 | 100 | 100 | 100 | 100 |

RESULTS:
EMULSIONS:

| 0-TIME | poor | | poor | | poor | | poor | |
|---|---|---|---|---|---|---|---|---|
| AFTER 20 TURNS | excellent | | excellent | | excellent | | poor | |
| AFTER 24 HOURS | good | | fair | | good | | poor | |
| SOLIDS OR CREAMS: | SUPER | PCPT | SUPER | PCPT | SUPER | PCPT | SUPER | PCPT |
| 0-TIME NO TURNS | 11 | | 14 | | 44 | | 12 | |
| 0-TIME 20 TURNS | 0 | | 1 | | 0 | | 15 | |
| ONE HOUR | 0 | | 8 | | 0 | | 15 | |
| TWO HOURS | 0.5 | | 8 | | 0.5 | | 15 | |
| FOUR HOURS | 0 | | 8 | | 2 | | 18 | |
| 24 HOURS | 11 | | 11 | | 10 | | 18 | |

| RUN NO. | 80 | | 81 | |
|---|---|---|---|---|
| COMPOSITION WT. % | DILUTION* | CONC. | DILUTION* | CONC. |
| LP-100 | 0 | 0 | 0 | 0 |
| LP-300 | 3.68 | 92 | 3.68 | 92 |
| EXXON 200 | 0 | 0 | 0 | 0 |
| GAFAC RE610 | 0 | 0 | 0.08 | 2 |
| IGEPAL CO630 | 0.12 | 3 | 0.04 | 1 |
| PROWL | 0.2 | 5 | 0.2 | 5 |
| HARD WATER | 96 | 0 | 96 | 0 |
| TOTAL | 100 | 100 | 100 | 100 |

RESULTS:
EMULSIONS:

| 0-TIME | poor | | poor | |
|---|---|---|---|---|
| AFTER 20 TURNS | poor | | poor | |
| AFTER 24 HOURS | poor | | poor | |
| SOLIDS OR CREAMS: | SUPER | PCPT | SUPER | PCPT |
| 0-TIME NO TURNS | 11 | | 11 | |
| 0-TIME 20 TURNS | 11 | | 15 | |
| ONE HOUR | 12 | | 15 | |
| TWO HOURS | 14 | | 16 | |
| FOUR HOURS | 14 | | 18 | |
| 24 HOURS | 15 | | 18 | |

*Diluted 2 to 50 grams. 10% runs were performed on selected blends and depicted in Table 3-B.

TABLE 3-B

10% PROWL

| RUN NO. | 82 | | 83 | | 84 | | 85 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 0.85 | 42.5 | 0.68 | 34 | 0.85 | 42.5 | 0.85 | 42.5 |
| LP-300 | 0.85 | 42.5 | 0.51 | 25.5 | 0 | 0 | 0 | 0 |
| EXXON 200 | 0 | 0 | 0.51 | 25.5 | 0.85 | 42.5 | 0.85 | 42.5 |
| GAFAC RE610 | 0.1 | 5 | 0.06 | 3 | 0.1 | 5 | 0.06 | 3 |
| IGEPAL CO630 | 0 | 0 | 0.04 | 2 | 0 | 0 | 0.04 | 2 |
| PROWL | 0.2 | 10 | 0.2 | 10 | 0.2 | 10 | 0.2 | 10 |
| HARD WATER | 98 | 0 | 98 | 0 | 98 | 0 | 98 | 0 |
| TOTAL | 100 | 100 | 100 | 100 | 100 | 100 | 100 | 100 |

RESULTS:
EMULSIONS:

| | | | | | | | | |
|---|---|---|---|---|---|---|---|---|
| 0-TIME | poor | | poor | | poor | | poor | |
| AFTER 20 TURNS | excellent | | excellent | | excellent | | excellent | |
| AFTER 24 HOURS | poor | | good | | good | | good | |

| SOLIDS OR CREAMS: | SUPER | PCPT | SUPER | PCPT | SUPER | PCPT | SUPER | PCPT |
|---|---|---|---|---|---|---|---|---|
| 0-TIME NO TURNS | 6 | 0 | 7 | 0 | 6 | 0 | 5 | 0 |
| 0-TIME 20 TURNS | 0 | 0 | 0 | 0 | 0 | 0 | 0 | 0 |
| ONE HOUR | 3 | 0 | 0 | 0 | 0 | 0 | 0 | 0 |
| TWO HOURS | 5 | 0 | 0.5 | 0 | 0 | 0 | 0 | 0 |
| FOUR HOURS | 6 | 0 | 0.5 | 0 | 0.5 | 0 | 0 | 0 |
| 24 HOURS | 10 | 0 | 4 | 0 | 3 | 0 | 3 | 0 |

| RUN NO. | 86 | | 87 | |
|---|---|---|---|---|
| COMPOSITION WT. % | DILUTED* | CONC. | DILUTED* | CONC. |
| LP-100 | 0 | 0 | 0 | 0 |
| LP-300 | 0.85 | 42.5 | 0.85 | 42.5 |
| EXXON 200 | 0.85 | 42.5 | 0.85 | 42.5 |
| GAFAC RE610 | 0.1 | 5 | 0.06 | 3 |
| IGEPAL CO630 | 0 | 0 | 0.04 | 2 |
| PROWL | 0.2 | 10 | 0.2 | 10 |
| HARD WATER | 98 | 0 | 98 | 0 |
| TOTAL | 100 | 100 | 100 | 100 |

RESULTS:
EMULSIONS:

| | | | | |
|---|---|---|---|---|
| 0-TIME | poor | | poor | |
| AFTER 20 TURNS | excellent | | excellent | |
| AFTER 24 HOURS | good | | good | |

| SOLIDS OR CREAMS: | SUPER | PCPT | SUPER | PCPT |
|---|---|---|---|---|
| 0-TIME NO TURNS | 7 | 0 | 6 | 0 |
| 0-TIME 20 TURNS | 0 | 0 | 0 | 0 |
| ONE HOUR | 0 | 0 | 0 | 0 |
| TWO HOURS | 1 | 0 | 0 | 0 |
| FOUR HOURS | 2 | 0 | 0.5 | 0 |
| 24 HOURS | 6 | 0 | 3 | 0 |

*Diluted 1 to 50 grams. 20% runs were performed on selected blends and depicted in Table 3-C.

TABLE 3-C

20% PROWL

| RUN NO. | 88 | | 89 | | 90 | |
|---|---|---|---|---|---|---|
| COMPOSITION WT. % | DILUTED* | CONC. | DILUTED* | CONC. | DILUTED* | CONC. |
| LP-100 | 0.3 | 30 | 0.375 | 37.5 | 0.375 | 37.5 |
| LP-300 | 0.225 | 22.5 | 0 | 0 | 0 | 0 |
| EXXON 200 | 0.225 | 22.5 | 0.375 | 37.5 | 0.375 | 37.5 |
| GAFAC RE610 | 0.03 | 3 | 0.05 | 5 | 0.03 | 3 |
| IGEPAL CO630 | 0.02 | 2 | 0 | 0 | 0.02 | 2 |
| PROWL | 0.2 | 20 | 0.2 | 20 | 0.2 | 20 |
| HARD WATER | 99 | 0 | 99 | 0 | 99 | 0 |
| TOTAL | 100 | 100 | 100 | 100 | 100 | 100 |

RESULTS:
EMULSIONS:

| | | | | | | |
|---|---|---|---|---|---|---|
| 0-TIME | poor | | fair | | fair | |
| AFTER 20 TURNS | excellent | | excellent | | excellent | |
| AFTER 24 HOURS | excellent | | excellent | | excellent | |

| SOLIDS OR CREAMS: | SUPER | PCT | SUPER | PCT | SUPER | PCT |
|---|---|---|---|---|---|---|
| 0-TIME NO TURNS | 7 | 0 | 0 | 3 | 0 | 3 |
| 0-TIME 20 TURNS | 0 | 0 | 0 | 0 | 0 | 0 |
| ONE HOUR | 0 | 0 | 0 | 0 | 0 | 0 |
| TWO HOURS | 0 | 0 | 0 | 0 | 0 | 0 |
| FOUR HOURS | 0 | 0 | 0 | 0.5 | 0 | 0.5 |

TABLE 3-C-continued

| | 20% PROWL | | | | | |
|---|---|---|---|---|---|---|
| 24 HOURS | 2 | 0 | 0 | 1 | 0 | 1 |

| RUN NO. | 91 | | 92 | |
|---|---|---|---|---|
| COMPOSITION WT. % | DILUTED* | CONC. | DILUTED* | CONC. |
| LP-100 | 0 | 0 | 0 | 0 |
| LP-300 | 0.375 | 37.5 | 0.375 | 37.5 |
| EXXON 200 | 0.375 | 37.5 | 0.375 | 37.5 |
| GAFAC RE610 | 0.05 | 5 | 0.03 | 3 |
| IGEPAL CO630 | 0 | 0 | 0.02 | 2 |
| PROWL | 0.2 | 20 | 0.2 | 20 |
| HARD WATER | 99 | 0 | 99 | 0 |
| TOTAL | 100 | 100 | 100 | 100 |

RESULTS:
EMULSIONS:

| | | |
|---|---|---|
| 0-TIME | poor | poor |
| AFTER 20 TURNS | excellent | excellent |
| AFTER 24 HOURS | excellent | excellent |

| SOLIDS OR CREAMS: | SUPER | PCPT | SUPER | PCPT |
|---|---|---|---|---|
| 0-TIME NO TURNS | 4 | 0 | 3 | 0 |
| 0-TIME 20 TURNS | 0 | 0 | 0 | 0 |
| ONE HOUR | 0 | 0 | 0 | 0 |
| TWO HOURS | 0 | 0 | 0 | 0 |
| FOUR HOURS | 0.5 | 0 | 0.5 | 0 |
| 24 HOURS | 2 | 0 | 2 | 0 |

*Diluted 0.5 to 50 grams.

TABLE 4

| | 20% PROWL | | | | | | | |
|---|---|---|---|---|---|---|---|---|
| RUN NO. | 93 | | 94 | | 95 | | 96 | |
| COMPONENT | DILUTED* | CONC. | DILUTED* | CONC. | DILUTED* | CONC. | DILUTED* | CONC. |
| NMP | 0 | 0 | 0 | 0 | 0 | 0 | 0 | 0 |
| LP-100 | 0.8125 | 32.5 | 0.8125 | 32.5 | 0.8125 | 32.5 | 0.8125 | 32.5 |
| EXXON 200 | 0.8125 | 32.5 | 0 | 0 | 0 | 0 | 0 | 0 |
| EXXAT 600 | 0 | 0 | 0.8125 | 32.5 | 0 | 0 | 0 | 0 |
| EXXAT 900 | 0 | 0 | 0 | 0 | 0.8125 | 32.5 | 0 | 0 |
| EXXAT 1300 | 0 | 0 | 0 | 0 | 0 | 0 | 0.8125 | 32.5 |
| GAFAC RE610 | 0.375 | 15 | 0.375 | 15 | 0.375 | 15 | 0.375 | 15 |
| PROWL | 0.5 | 20 | 0.5 | 20 | 0.5 | 20 | 0.5 | 20 |
| HARD WATER | 97.5 | | 97.5 | | 97.5 | | 97.5 | |
| TOTAL | 100 | 100 | 100 | 100 | 100 | 100 | 100 | 100 |

RESULTS:
EMULSIONS:

| | | | | |
|---|---|---|---|---|
| 0-TIME | fair | poor | poor | poor |
| AFTER 20 TURNS | excellent | excellent | excellent | excellent |
| AFTER 24 HOURS | | | | |

| SOLIDS OR CREAMS: | SUPER | PCPT | SUPER | PCPT | SUPER | PCPT | SUPER | PCPT |
|---|---|---|---|---|---|---|---|---|
| 0-TIME NO TURNS | | | | | | | | |
| 0-TIME 20 TURNS | 0 | | 0 | | 0 | | 0 | |
| ONE HOUR | 0 | | 0.5 | | 0 | | 0 | |
| TWO HOURS | | 0.5 | 0.5 | | 0 | | 0 | |
| FOUR HOURS | | 1 | 0.5 | | 0 | | 0 | |
| 24 HOURS | | 1.5 | | | 0 | | 0 | |

| RUN NO. | 97 | | 98 | | 99 | | 100 | |
|---|---|---|---|---|---|---|---|---|
| COMPONENT | DILUTED* | CONC. | DILUTED* | CONC. | DILUTED* | CONC. | DILUTED* | CONC. |
| NMP | 0 | 0 | 0 | 0 | 0 | 0 | 0.599 | 23.96 |
| LP-100 | 0.65 | 26 | 0.65 | 26 | 0.8125 | 32.5 | 0.449 | 17.96 |
| EXXON 200 | 0.65 | 26 | 0.4875 | 19.5 | 0.325 | 13 | 0.449 | 17.96 |
| EXXAT 600 | 0.325 | 13 | 0 | 0 | 0 | 0 | 0 | 0 |
| EXXAT 900 | 0 | 0 | 0.4875 | 19.5 | 0 | 0 | 0 | 0 |
| EXXAT 1300 | 0 | 0 | 0 | 0 | 0.4875 | 19.5 | 0 | 0 |
| GAFAC RE610 | 0.375 | 15 | 0.375 | 15 | 0.375 | 15 | 0.35925 | 14.37 |
| PROWL | 0.5 | 20 | 0.5 | 20 | 0.5 | 20 | 0.64375 | 25.75 |
| HARD WATER | 97.5 | | 97.5 | | 97.5 | | 97.5 | |
| TOTAL | 100 | 100 | 100 | 100 | 100 | 100 | 100 | 100 |

RESULTS:
EMULSIONS:

| | | | | |
|---|---|---|---|---|
| 0-TIME | good | fair | poor | excellent |
| AFTER 20 TURNS | excellent | excellent | excellent | excellent |
| AFTER 24 HOURS | | | | |

| SOLIDS OR CREAMS: | SUPER | PCPT | SUPER | PCPT | SUPER | PCPT | SUPER | PCPT |
|---|---|---|---|---|---|---|---|---|

TABLE 4-continued

20% PROWL

| | | | | |
|---|---|---|---|---|
| 0-TIME NO TURNS | | | | |
| 0-TIME 20 TURNS | 0 | 0 | 0 | 0 |
| ONE HOUR | 0 | 0 | 0 | 0 |
| TWO HOURS | 0.5 | 0 | 0.5 | 0 |
| FOUR HOURS | 0.5 | 0 | 0.5 | 0 |
| 24 HOURS | 0.5 | 0 | 0.5 | 0 |

*Diluted 1.25 to 50 grams.

TABLE 5

10% CGA

| RUN NO. | 100 | | 101 | | 102 | | 103 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 1.06 | 53 | 1.06 | 53 | 0.54 | 27 | 0.54 | 27 |
| LP-940 | 0.54 | 27 | 0.54 | 27 | 0.26 | 13 | 0.26 | 13 |
| EXXON 200 | 0 | 0 | 0 | 0 | 0.8 | 40 | 0.8 | 40 |
| GAFAC RE610 | 0.2 | 10 | 0.1 | 5 | 0.1 | 5 | 0.1 | 5 |
| IGEPAL CO630 | 0 | 0 | 0.1 | 5 | 0.1 | 5 | 0.1 | 5 |
| CGA 184699 | 0.2 | 10 | 0.2 | 10 | 0.2 | 10 | 0.2 | 10 |
| HARD WATER | 98 | 0 | 98 | 0 | 98 | 0 | 98 | 0 |
| TOTAL | 100 | 100 | 100 | 100 | 100 | 100 | 100 | 100 |

RESULTS:
EMULSIONS:

| | | | | | | | | |
|---|---|---|---|---|---|---|---|---|
| 0-TIME | poor | | poor | | good | | fair | |
| AFTER 20 TURNS | excellent | | excellent | | excellent | | excellent | |
| AFTER 24 HOURS | | | | | | | | |

| SOLIDS OR CREAMS: | SUPER | PCPT | SUPER | PCPT | SUPER | PCPT | SUPER | PCPT |
|---|---|---|---|---|---|---|---|---|
| 0-TIME NO TURNS | 8 | 1 | 8 | 0 | 0 | 3 | 0 | 3 |
| 0-TIME 20 TURNS | | | | | | | | |
| ONE HOUR | 4 | | 9 | | | 0.5 | | 0.5 |
| TWO HOURS | 4 | | 10 | | | 0.5 | | 0.5 |
| FOUR HOURS | 6 | | 11 | | | 1 | | 1 |
| 24 HOURS | 26 | | 13 | | | 6 | | 6 |

| RUN NO. | 104 | | 105 | | 106 | | 107 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 0.8 | 40 | 0.8 | 40 | 1.34 | 67 | 1.34 | 67 |
| LP-940 | 0.4 | 20 | 0.4 | 20 | 0.26 | 13 | 0.26 | 13 |
| EXXON 200 | 0.4 | 20 | 0.4 | 20 | 0 | 0 | 0 | 0 |
| GAFAC RE610 | 0.2 | 10 | 0.1 | 5 | 0.2 | 10 | 0.1 | 5 |
| IGEPAL CO630 | 0 | 0 | 0.1 | 5 | 0 | 0 | 0.1 | 5 |
| CGA 184699 | 0.2 | 10 | 0.2 | 10 | 0.2 | 10 | 0.2 | 10 |
| HARD WATER | 98 | 0 | 98 | 0 | 98 | 0 | 98 | 0 |
| TOTAL | 100 | 100 | 100 | 100 | 100 | 100 | 100 | 100 |

RESULTS:
EMULSIONS:

| | | | | | | | | |
|---|---|---|---|---|---|---|---|---|
| 0-TIME | poor | | poor | | poor | | poor | |
| AFTER 20 TURNS | excellent | | excellent | | excellent | | excellent | |
| AFTER 24 HOURS | | | | | | | | |

| SOLIDS OR CREAMS: | SUPER | PCPT | SUPER | PCPT | SUPER | PCPT | SUPER | PCPT |
|---|---|---|---|---|---|---|---|---|
| 0-TIME NO TURNS | 11 | 2 | 8 | 0 | 7 | 0 | 7 | 0 |
| 0-TIME 20 TURNS | | | | | | | | |
| ONE HOUR | 0 | | 0 | | 5 | | 7 | |
| TWO HOURS | 0 | | 0 | | 7 | | 8 | |
| FOUR HOURS | 0 | | 2 | | 13 | | 8 | |
| 24 HOURS | 0.5 | | 3 | | 16 | | 10 | |

| RUN NO. | 108 | | 109 | | 110 | | 111 | |
|---|---|---|---|---|---|---|---|---|
| COMPOSITION WT. % | DILUTED* | CONC. | DILUTED* | CONC. | DILUTED* | CONC. | DILUTED* | CONC. |
| LP-100 | 0.66 | 33 | 0.66 | 33 | 1 | 50 | 1 | 50 |
| LP-940 | 0.14 | 7 | 0.14 | 7 | 0.2 | 10 | 0.2 | 10 |
| EXXON 200 | 0.8 | 40 | 0.8 | 40 | 0.4 | 20 | 0.4 | 20 |
| GAFAC RE610 | 0.2 | 10 | 0.1 | 5 | 0.2 | 10 | 0.1 | 5 |
| IGEPAL CO630 | 0 | 0 | 0.1 | 5 | 0 | 0 | 0.1 | 5 |
| CGA 184699 | 0.2 | 10 | 0.2 | 10 | 0.2 | 10 | 0.2 | 10 |
| HARD WATER | 98 | 0 | 98 | 0 | 98 | 0 | 98 | 0 |
| TOTAL | 100 | 100 | 100 | 100 | 100 | 100 | 100 | 100 |

RESULTS:
EMULSIONS:

| | | | | | | | | |
|---|---|---|---|---|---|---|---|---|
| 0-TIME | fair/good | | fair/good | | poor | | poor | |
| AFTER 20 TURNS | excellent | | excellent | | excellent | | excellent | |
| AFTER 24 HOURS | | | | | | | | |

TABLE 5-continued

| | 10% CGA | | | | | | | |
|---|---|---|---|---|---|---|---|---|
| SOLIDS OR CREAMS: | SUPER | PCPT | SUPER | PCPT | SUPER | PCPT | SUPER | PCPT |
| 0-TIME NO TURNS | 0 | 2 | 0 | 3 | 1 | 5 | 10 | 1 |
| 0-TIME 20 TURNS | | | | | | | | |
| ONE HOUR | | 0 | | 0.5 | | 0 | | 0 |
| TWO HOURS | | 0.5 | | 0.5 | | 0 | | 0 |
| FOUR HOURS | | 0.5 | | 1 | | 0 | | 0 |
| 24 HOURS | | 2 | | 3 | | 0.5 | | 4 |

*Diluted 1 to 50 grams.

TABLE 6

E.C. FORMULATION

| RUN NO. | 112 | | 113 | | 114 | | 115 | |
|---|---|---|---|---|---|---|---|---|
| COMPOSITION NO. | DILUTED* | CONC. | DILUTED* | CONC. | DILUTED* | CONC. | DILUTED* | CONC. |
| LP-100 | 1.25 | 60 | 1.25 | 60 | 1.35 | 65 | 1.35 | 65 |
| LP-300 | 0.00 | 0 | 0.00 | 0 | 0.00 | 0 | 0.00 | 0 |
| EXXON 100 | 0.52 | 25 | 0.42 | 20 | 0.40 | 19 | 0.31 | 15 |
| GAFAC RM 710 | 0.06 | 3 | 0.17 | 8 | 0.08 | 4 | 0.17 | 8 |
| DIURON | 0.08 | 4 | 0.08 | 4 | 0.08 | 4 | 0.08 | 4 |
| THIDIAZURON | 0.17 | 8 | 0.17 | 8 | 0.17 | 8 | 0.17 | 8 |
| HARD WATER | 97.92 | 0 | 97.92 | 0 | 97.92 | 0 | 97.92 | 0 |
| TOTAL | 100.00 | 100 | 100.00 | 100 | 100.00 | 100 | 100.00 | 100 |

RESULTS:
EMULSIONS:

| | | | | |
|---|---|---|---|---|
| APPEARANCE | grey white | grey white | grey white | grey white |
| EMULSION BLOOM | excellent | excellent | excellent | fair |
| EMULSION STABILITY | fair | good | fair | good |
| EC THERMAL STABILITY | >4 weeks | >4 weeks | >4 weeks | >4 weeks |
| EMULSION CRYSTALLIZATION OF ACTIVES 24 HRS | none | none | none | none |

| RUN NO. | 116 | | 117 | |
|---|---|---|---|---|
| COMPOSITION NO. | DILUTED* | CONC. | DILUTED* | CONC. |
| LP-100 | 1.35 | 65 | 0.00 | 0 |
| LP-300 | 0.00 | 0 | 1.25 | 60 |
| EXXON 100 | 0.17 | 8 | 0.51 | 24.5 |
| GAFAC RM 710 | 0.31 | 15 | 0.07 | 3.5 |
| DIURON | 0.08 | 4 | 0.08 | 4 |
| THIDIAZURON | 0.17 | 8 | 0.17 | 8 |
| HARD WATER | 97.92 | 0 | 97.92 | 0 |
| TOTAL | 100.00 | 100 | 100.00 | 100 |

RESULTS:
EMULSIONS:

| | | |
|---|---|---|
| APPEARANCE | grey white | grey white |
| EMULSION BLOOM | poor | good |
| EMULSION STABILITY | excellent | fair |
| EC THERMAL STABILITY | >4 weeks | >4 weeks |
| EMULSION CRYSTALLIZATION OF ACTIVES 24 HRS | none | none |

*1 ml of concentrate was diluted to 47 ml.

What is claimed is:

1. A stable emulsifiable concentrate comprising a herbicide which is substantially insoluble in water, an organic diluent, a surfactant and a solvent composed of a component being selected from the group consisting of pyrrolidones having the formula

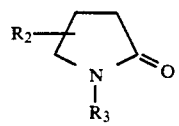

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14; alkyl gamma-butyrolactones, alkyl cyclic carbonates, and combinations thereof, wherein the alkyl portion may be distributed at one or more sites on the ring so long as one portion contains at least 6 carbon atoms and the total number of alkyl carbon atoms does not exceed 14, said component being present in an amount, in conjunction with a surfactant, effective to disperse the herbicide.

2. The concentrate of claim 1 wherein the component is selected from the group consisting of octylpyrrolidone, dodecylpyrrolidone, N-(2'-ethylhexylpyrrolidone), and mixtures thereof.

3. The concentrate of claim 1 wherein the organic diluent is an oil having a fractional dispersive solubility parameter of a greater than about 70% and a molar volume of greater than about 90 cm³/mole.

4. The concentrate of claim 3 wherein the diluent is selected from the group consisting of soybean oil, rape seed oil, long chain alcohols, long chain ketones, long chain esters, and ethers, and aromatic petroleum oils.

5. The concentrate of claim 4 wherein the diluent is an aromatic petroleum oil comprising about 60% of heavy aromatic solvent naphtha and about 40% of middle distillate solvent extractant.

6. The concentrate of claim 1 wherein the herbicide is selected from the group consisting of phenoxy compounds, benzoic acid, acetic acid, phthalic acid, aniline derivatives, nitriles, amides, acetamides, anilides, carbamates, thiocarbamates, heterocyclic nitrogen derivatives, urea derivatives, and phosphates.

7. The concentrate of claim 1 the amount of solvent is in the range from about 20 to 90%, and the amount of diluent is in the range from about 80 to 10%, each amount being based on the total weight of solvent and diluent in the concentrate.

8. The concentrate of claim 1 wherein the amount of surfactant is from about 1 to 25% by weight based on the total weight of the concentrate.

9. The concentrate of claim 8 wherein the concentration of the herbicide is in excess of about 5 weight percent. based on the weight of the total concentrate.

10. The concentrate of claim 9 wherein the amount of the herbicide is from about 5% to 25% by weight based on the total weight of the concentrate.

11. A composition comprising the emulsifiable concentrate of claim 1 wherein the herbicide is present in an effective herbicidal amount.

12. The composition of claim 11 wherein the concentration of the herbicide is in the range from about 10 ppm to 2 percent by weight.

13. A stable emulsifiable concentrate comprising a herbicide which is substantially insoluble in water, an aromatic petroleum oil comprising about 60% of heavy aromatic solvent naphtha and about 40% of middle distillate solvent extractant as a diluent, a surfactant and a solvent composed of a component being selected from the group consisting of pyrrolidones having the formula

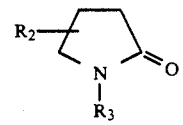

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14; and being present in an amount, in conjunction with a surfactant, effective to disperse the herbicide.

* * * * *